(12) United States Patent
Günther et al.

(10) Patent No.: US 11,583,513 B2
(45) Date of Patent: Feb. 21, 2023

(54) SEMIFLUORINATED ALKANE COMPOSITIONS

(71) Applicant: Novaliq GmbH, Heidelberg (DE)

(72) Inventors: Bernhard Günther, Dossenheim (DE); Dieter Scherer, Laufen (CH); Anthony Pettigrew, Heidelberg (DE)

(73) Assignee: NOVALIQ GMBH, Heidelberg (DE)

(*) Notice: Subject to any disclaimer, the term of this patent is extended or adjusted under 35 U.S.C. 154(b) by 43 days.

(21) Appl. No.: 16/783,972

(22) Filed: Feb. 6, 2020

(65) Prior Publication Data

US 2020/0246463 A1 Aug. 6, 2020

Related U.S. Application Data

(60) Division of application No. 16/041,317, filed on Jul. 20, 2018, now Pat. No. 10,576,154, which is a continuation of application No. 15/428,031, filed on Feb. 8, 2017, now Pat. No. 10,058,615, which is a continuation of application No. 14/427,969, filed as application No. PCT/EP2013/068909 on Sep. 12, 2013, now Pat. No. 9,770,508.

(30) Foreign Application Priority Data

Sep. 12, 2012 (EP) ..................... 12183997
May 27, 2013 (EP) ..................... 13169399

(51) Int. Cl.

| | | |
|---|---|---|
| *A61K 31/351* | (2006.01) | |
| *A61K 45/06* | (2006.01) | |
| *A61K 9/00* | (2006.01) | |
| *A61K 9/08* | (2006.01) | |
| *C08L 27/12* | (2006.01) | |
| *A61K 8/69* | (2006.01) | |
| *A61K 33/16* | (2006.01) | |
| *A61K 31/436* | (2006.01) | |
| *A61K 31/07* | (2006.01) | |
| *A61K 31/11* | (2006.01) | |
| *A61K 31/202* | (2006.01) | |
| *A61K 31/203* | (2006.01) | |
| *A61K 31/232* | (2006.01) | |
| *A61K 31/4418* | (2006.01) | |
| *C09K 15/00* | (2006.01) | |
| *C08F 14/26* | (2006.01) | |
| *A61K 47/06* | (2006.01) | |
| *A61K 31/02* | (2006.01) | |
| *A61P 27/02* | (2006.01) | |
| *A61P 27/04* | (2006.01) | |

(52) U.S. Cl.

CPC .......... *A61K 31/351* (2013.01); *A61K 9/0048* (2013.01); *A61K 9/08* (2013.01); *A61K 31/02* (2013.01); *A61K 31/07* (2013.01); *A61K 31/11* (2013.01); *A61K 31/202* (2013.01); *A61K 31/203* (2013.01); *A61K 31/232* (2013.01); *A61K 31/436* (2013.01); *A61K 31/4418* (2013.01); *A61K 45/06* (2013.01); *A61K 47/06* (2013.01); *C08F 14/26* (2013.01); *C09K 15/00* (2013.01); *A61P 27/02* (2018.01); *A61P 27/04* (2018.01)

(58) Field of Classification Search

CPC ............. C09K 15/00–04; A61K 31/07; A61K 31/202; A61K 31/203; A61K 2800/52; A61K 47/06; A61K 47/32; A61K 33/16; A61K 8/69; A61K 31/351; C08F 10/02; C08F 14/26; C08F 114/26; C08F 110/02; C08F 210/02; C08F 214/26; C08L 7/18; C08L 27/12–20; A23V 2250/211

See application file for complete search history.

(56) References Cited

U.S. PATENT DOCUMENTS

| | | |
|---|---|---|
| 2,616,927 A | 11/1952 | Kauck et al. |
| 4,452,818 A | 6/1984 | Haidt |
| 5,077,036 A | 12/1991 | Long, Jr. |
| 5,126,127 A | 6/1992 | Bhagwat et al. |
| 5,152,997 A | 10/1992 | Ebert et al. |
| 5,254,338 A | 10/1993 | Sakai et al. |
| 5,326,566 A | 7/1994 | Parab |
| 5,336,175 A | 8/1994 | Mames |
| 5,370,313 A | 12/1994 | Beard |
| 5,518,731 A | 5/1996 | Meadows |
| 5,667,809 A | 9/1997 | Trevino et al. |
| 5,849,291 A | 12/1998 | Kessler |
| 5,851,544 A | 12/1998 | Penska et al. |

(Continued)

FOREIGN PATENT DOCUMENTS

| | | |
|---|---|---|
| CN | 200977281 Y | 11/2007 |
| CN | 202136470 U | 2/2012 |

(Continued)

OTHER PUBLICATIONS

Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.

(Continued)

*Primary Examiner* — Theodore R. Howell

(74) *Attorney, Agent, or Firm* — Hoxie & Associates LLC

(57) ABSTRACT

The invention provides novel compositions comprising semifluorinated alkanes and at least one compound sensitive or prone to oxidation. The compositions can be used as medicines that are topically administered to an eye or ophthalmic tissue. The invention further provides kits comprising such compositions.

12 Claims, No Drawings

(56) References Cited

U.S. PATENT DOCUMENTS

| | | |
|---|---|---|
| 5,874,469 A | 2/1999 | Maniar et al. |
| 5,874,481 A | 2/1999 | Weers |
| 5,980,936 A | 11/1999 | Krafft et al. |
| 5,981,607 A | 11/1999 | Ding |
| 6,042,845 A | 3/2000 | Sun et al. |
| 6,060,085 A | 5/2000 | Osborne |
| 6,113,919 A | 9/2000 | Reiss et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,335,335 B2 | 1/2002 | Higashiyama et al. |
| 6,372,243 B2 | 4/2002 | Kobuch |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz |
| 7,001,607 B1 | 2/2006 | Menz |
| 7,026,359 B2 | 4/2006 | Gross |
| 7,258,869 B1 | 8/2007 | Berry |
| 7,740,875 B2 | 6/2010 | Dechow |
| 8,029,977 B2 | 10/2011 | Meinert |
| 8,222,292 B2 | 7/2012 | Goskonda et al. |
| 8,470,873 B2 | 6/2013 | Chen |
| 8,614,178 B2 | 12/2013 | Theisinger et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Günther et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 10,045,996 B2 | 8/2018 | Theisinger et al. |
| 10,507,132 B2 | 12/2019 | Graf et al. |
| 10,813,976 B2 * | 10/2020 | Löscher et al. |
| 10,813,999 B2 * | 10/2020 | Gunther .......... A61P 17/10 |
| 2002/0004063 A1 | 1/2002 | Zhang |
| 2002/0006442 A1 | 1/2002 | Mishra et al. |
| 2002/0064565 A1 | 5/2002 | Karagoezian |
| 2002/0128527 A1 | 9/2002 | Meinert |
| 2002/0137793 A1 | 9/2002 | Klimko |
| 2003/0018044 A1 | 1/2003 | Peyman |
| 2003/0027833 A1 | 2/2003 | Cleary et al. |
| 2003/0194447 A1 | 10/2003 | Scholz et al. |
| 2003/0170194 A1 | 11/2003 | Piotrowiak |
| 2004/0044045 A1 | 3/2004 | Burk |
| 2004/0082660 A1 | 4/2004 | Ueno |
| 2004/0101551 A1 | 5/2004 | Selzer |
| 2004/0265362 A1 | 12/2004 | Susilo |
| 2004/0266702 A1 | 12/2004 | Dawson et al. |
| 2005/0079210 A1 | 4/2005 | Gupta |
| 2005/0084553 A1 | 4/2005 | Moon et al. |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0153905 A1 | 7/2006 | Carrara et al. |
| 2008/0050335 A1 | 2/2008 | Faour et al. |
| 2008/0112895 A1 | 5/2008 | Kottayil et al. |
| 2008/0153909 A1 | 6/2008 | Dana et al. |
| 2008/0207217 A1 | 8/2008 | Turner et al. |
| 2008/0234389 A1 | 9/2008 | Mecozzi et al. |
| 2008/0260656 A1 | 10/2008 | Mallard |
| 2009/0136430 A1 | 5/2009 | Dugger |
| 2009/0149546 A1 | 6/2009 | Chang |
| 2009/0169601 A1 | 7/2009 | Koch et al. |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0137252 A1 | 6/2010 | Matsumura et al. |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0053242 A1 | 3/2012 | Cela Lopez |
| 2012/0095097 A1 | 4/2012 | Tabuchi et al. |
| 2012/0100183 A1 | 4/2012 | Schlessinger et al. |
| 2012/0219640 A1 | 8/2012 | Wright |
| 2012/0238639 A1 | 9/2012 | Theisinger et al. |
| 2012/0244177 A1 | 9/2012 | Theisinger et al. |
| 2013/0011484 A1 | 1/2013 | Bevier |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0186350 A1 | 7/2014 | Ghosh et al. |
| 2014/0303219 A1 | 10/2014 | Bingaman et al. |
| 2014/0369993 A1 | 12/2014 | Günther et al. |
| 2015/0045282 A1 | 2/2015 | Elsohly et al. |
| 2015/0099019 A1 | 4/2015 | Johnson |
| 2015/0224064 A1 | 8/2015 | Günther et al. |
| 2015/0238605 A1 | 8/2015 | Günther et al. |
| 2015/0258040 A1 | 9/2015 | Lynch et al. |
| 2016/0101178 A1 | 4/2016 | Wilson |
| 2016/0159902 A1 | 6/2016 | Günther et al. |
| 2016/0184259 A1 | 6/2016 | Anastassov et al. |
| 2016/0243189 A1 | 8/2016 | Gu et al. |
| 2017/0020726 A1 | 1/2017 | Labombarbe et al. |
| 2017/0044096 A1 | 2/2017 | Laskin et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2017/0216204 A1 | 8/2017 | Theisinger et al. |
| 2017/0224531 A1 | 8/2017 | Chauhan et al. |
| 2018/0360908 A1 | 12/2018 | Beier et al. |
| 2019/0274970 A1 | 9/2019 | Günther et al. |
| 2019/0328717 A1 | 10/2019 | Günther et al. |
| 2019/0343793 A1 | 11/2019 | Günther et al. |
| 2020/0060987 A1 | 2/2020 | Gunther et al. |
| 2020/0129543 A1 | 4/2020 | Löscher et al. |
| 2022/0079925 A1 | 3/2022 | Günther et al. |

FOREIGN PATENT DOCUMENTS

| | | |
|---|---|---|
| CN | 203524843 U | 4/2014 |
| EP | 0 089 815 | 9/1983 |
| EP | 0 593 552 | 4/1994 |
| EP | 0 670 159 | 9/1995 |
| EP | 0 965 329 | 12/1999 |
| EP | 0 965 334 | 12/1999 |
| EP | 0 939 655 | 6/2002 |
| EP | 1 152 749 | 4/2006 |
| EP | 2 110 126 | 10/2009 |
| EP | 2 332 525 | 6/2011 |
| EP | 2 335 735 | 6/2011 |
| EP | 2 462 921 | 6/2012 |
| JP | S6452722 | 2/1989 |
| JP | H0764702 B2 | 7/1995 |
| JP | 2000511157 | 8/2000 |
| JP | 2001/158734 | 6/2001 |
| JP | 2008/505177 | 2/2008 |
| JP | 2011/006348 | 1/2011 |
| JP | 2011/024841 A | 2/2011 |
| WO | WO 1995/033447 | 12/1995 |
| WO | WO 96/40052 | 12/1996 |
| WO | WO 97/12852 | 4/1997 |
| WO | WO 1998/005301 | 12/1998 |
| WO | WO 00/10531 | 3/2000 |
| WO | WO 00/24376 | 5/2000 |
| WO | WO 00/54588 | 9/2000 |
| WO | WO 02/49631 | 6/2002 |
| WO | WO 03/099258 | 12/2003 |
| WO | WO 2005/018530 A2 | 3/2005 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |

(56) References Cited

FOREIGN PATENT DOCUMENTS

| WO | WO 2006/042059 | 4/2006 | | |
|---|---|---|---|---|
| WO | WO 2006/048242 | 5/2006 | | |
| WO | WO 2007/008666 | 1/2007 | | |
| WO | WO 2007/052288 | 5/2007 | | |
| WO | WO 2008/060359 | 5/2008 | | |
| WO | WO 2009/013435 | 1/2009 | | |
| WO | WO 2009/065565 | 5/2009 | | |
| WO | WO 2010/062394 | 6/2010 | | |
| WO | WO 2010/146536 | 12/2010 | | |
| WO | WO 2011/009436 | 1/2011 | | |
| WO | WO 2011/073134 | 6/2011 | | |
| WO | WO 2011/113855 | 9/2011 | | |
| WO | WO-2011151079 A2 * | 12/2011 | ............ | A61K 47/06 |
| WO | WO 2012/052418 | 4/2012 | | |
| WO | WO 2012/062834 | 5/2012 | | |
| WO | WO 2012/093113 | 7/2012 | | |
| WO | WO 2012/121754 | 9/2012 | | |
| WO | WO 2012/160179 | 11/2012 | | |
| WO | WO 2012/160180 | 1/2013 | | |
| WO | WO 2013/110621 | 8/2013 | | |
| WO | WO 2014/041055 | 4/2014 | | |
| WO | WO 2014/041071 | 4/2014 | | |
| WO | WO 2014/154531 | 10/2014 | | |
| WO | WO 2015/011199 | 1/2015 | | |
| WO | WO 2016/025560 | 2/2016 | | |
| WO | WO 2018/115097 | 6/2018 | | |

OTHER PUBLICATIONS

Deschamps, J. et al., "Solubility of oxygen, carbon dioxide and water in semifluorinated alkanes and in perfluorooctylbromide by molecular simulation", Journal of Fluorine Chemistry, Elsevier, vol. 125, No. 3, 2004.
JPH0764702B2, Kanebo Ltd, "Cosmetic of Polyphasic Emulsion Type," Jul. 12, 1995, English language machine translation of abstract, Espacenet, date obtained: Apr. 30, 2021, 1 page <https://worldwide.espacenet.com/patent/search/family/014142733/publication/JPH0764702B2?q=JPH0764702B2>.
Matteucci et al., "Biocompatibility assessment of liquid artificial vitreous replacements: relevance of in vitro studies," Survey of Ophthalmology, 2007, 52(3):289-299, Abstract Only (1 page).
Yaoxue Zhuanye Zhishi II (Editor: Jin Xiangqun), Military Medical Science Press, 1st Printing of 2nd Edition, Mar. 2009, p. 158.
Yaoxue Zhuanye Zhishi II (Editor: Jin Xiangqun), Military Medical Science Press, 1st Printing of 2nd Edition, Mar. 2009, p. 158, 3 pages (English Machine Translation).
Ahmed, et al., "Disposition of Timolol and Inulin in the Rabbit Eye Following Corneal Versus Non-Corneal Absorption," International Journal of Pharmaceutics, 1987, 38:9-21.
Bardin et al., "Long-Range Nanometer-Scale Organization of Semifluorinated Alkane Monolayers at the Air/Water Interface," Langmuir, 2011, 27:13497-13505.
Blackie et al., "MGD: Getting to the Root Cause of Dry Eye", Review of Optometry, 2012, pp. 1-12.
Broniatowski, M. et al., "Langmuir Monolayers Characteristics of Perfluorodecyl)-Alkanes," Journal of Physical Chemistry B, 2004, 108:13403-13411.
Chhadva et al., "Meibomian Gland Disease the Role of Gland Dysfunction in Dry Eye Disease," Ophthalmology (2017) 124(11 Supplement): S20-S26.
Chemical Book, "5-Fluorouracil," available at http://www.chemicalbook.com/-ChemicalProductProperty_EN_CB8162744.htm>, accessed Mar. 7, 2014.
Costa Gomes et al., "Solubility of dioxygen in seven fluorinated liquids," Journal of Fluorine Chemistry, 2004, 125:1325-1329.
Davies, N., "Biopharmaceutical Considerations in Topical Ocular Drug Delivery," Clinical and Experimental Pharmacology and Physiology, 2000, 27:558-562.
Dembinski et al., Semi-fluorinated Alkanes as Carriers for Drug Targeting in Acute Respiratory Failure, Experimental Lung Research, 2010, 36(8):499-507.
Dias et al., "Solubility of oxygen in liquid perfluorocarbons," Fluid Phase Equilibria, 2004, 222-223:325-330.
Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).
English-language machine translation of EP0670159 (A1) issued in U.S. Appl. No. 14/122,025 on Apr. 1, 2015, 10 pages.
Freiburger Dokumentenserver (FreiDok), Albert-Ludwigs, Unversitat Feiburg im Breisgau, retrieved from http://www.freidok.uni-freiburg.de/volltexte/5682, retrieved on Feb. 5, 2014, 2 pages.
Gayton, J., "Etiology, Prevalence, and Treatment of Dry Eye Disease," Clinical Ophthalmology, 2009, 3:405-412.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).
Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).
Gerdenitsch, "Emulsions—established and promising drug carriers for parenteral adminstration", retrieved from internet: http:/ipimediaworld.com/wp-content/uploads/2012/05/Pages-from-IPI-Volume-2-Issue- 1-11.pdf. Date Accessed: Jul. 20, 2016.
German, E.J., et al., "Reality of drop size from multi-dose eye drop bottles: is it cause for concern?" Eye, 1999, 13:93-100.
Griffin, W., "Classification of Surface-Active Agnets by 'HLB'," Journal of the Society of Cosmetic Chemists, 1949, 1:311-326.
Hardung, H., "Semifluorierte und perfluorierte Vergindungen zur topischen und parenteralen Anwendung," 2008, retrieved from http://www.freidok.uni-freiburg.de/volltexte/5682/pdf/Dissertation_Hardung.pdf; Retrieved Oct. 10, 2011.
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5):373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
International Preliminary Report on Patentability dated Sep. 18, 2012, for International Patent Application PCT/EP2011/053949, 9 Pages.
International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Preliminary Report on Patentability for International Application No. PCT/EP2011/068141 dated Apr. 23, 2013, 4 pages.
International Preliminary Report on Patentability for International Application No. PCT/EP2011/069795 dated May 14, 2013, 8 pages.
International Preliminary Report on Patentability for International Application No. PCT/EP2012/050043 dated Jul. 10, 2013, 5 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 7 pages.
International Preliminary Report on Patentability for International Application No. PCT/EP2013/051163 dated Jul. 29, 2014, 7 pages.
International Preliminary Report on Patentability dated Jan. 26, 2016, for International Application No. PCT/EP2014/065840, 11 pages.

(56) References Cited

OTHER PUBLICATIONS

International Search Report for International Application No. PCT/EP2011/053949 dated Sep. 6, 2011, 5 pages.
International Search Report for International Application No. PCT/EP2011/068141 dated Dec. 14, 2011, 2 pages.
International Search Report for International Application No. PCT/EP2011/069795 dated Jan. 16, 2012, 3 pages.
International Search Report for International Application No. PCT/EP2012/050043 dated Apr. 24, 2012, 2 pages.
International Search Report for International Application No. PCT/EP2012/059787 dated Dec. 5, 2012, 4 pages.
International Search Report for International Application No. PCT/EP2012/059788 dated Dec. 3, 2012, 4 pages.
International Search Report for International Application No. PCT/EP2013/051163 dated Mar. 4, 2013, 4 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
Ishizaki et al., "Treatment of Diabetic Retinopathy," Forum: Complication, Practice, 2009, 26(5): 474-476 (3 pages).
JP 2000511157 A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed: Feb. 10, 2016.
Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7):1090-1095.
Kociok, N., et al, "Influence on Membrane-Mediated Cell Activation by Vesicles of Silicone Oil or Perfluorohexyloctane," Graefe's Archive for Clinical and Experimental Ophthalmology, 2005, 243:345-358.
Lallemand et al., "Cyclosporine a delivery to the eye: a pharmaceutical challenge," European Journal of Pharmaceutics and Biopharmaceutics, 2003, 56(3):307-318, Abstract Only (1 page).
Lemp, M., Management of Dry Eye Disease, The American Journal of Managed Care, 2008, 14 (3):S88-S101.
Mackiewicz, J., "In Vivo Retinal Tolerance of Various Heavy Silicone Oils," Investigative Ophthalmology & Visual Science, 2007, 48 (4):1873-1883.
Meinert, H. et al., "The Use of Semifluorinated Alkanes in Blood-Substitutes," Biomaterials, Artificial Cells, and Immobilization Biotechnology, 1993, 21 (5):583-595.
Meinert, H. et al., "Semifluorinated Alkanes—A New Class of Compounds with Outstanding Properties for Use in Ophthalmology," European Journal of Ophthalmology, 2000, 10 (3):189-197.
Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation of Abstract, p. 138.
Messmer, E.M., "The Pathophysiology, Diagnosis, and Treatment of Dry Eye Disease," (2015) Deutsches Arzteblatt International, 112(5):71-82.
Murdan, S., "Enhancing the Nail Permeability of Topically Appied Drugs," Expert Opinion on Drug Delivery, 2008, 5 (11):1267-1282.
O'Ourke, M. et al., "Enhancing Delivery of Topical Ocular Drops," Cataract & Refractive Surgery Today Europe, 2016, 2 pages.
Perry, H., "Dry Eye Disease: Pathophysiology, Classification, and Diagnosis," The American Journal of Managed Care, 2008, 14 (3):S79-S87.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Pinarci, E. et al., "Intraocular Gas Application in the Diagnosis and Treatment of Valsalva Retiopathy in Case with Premacular Hemorrhage," XP002625604, Retina Vitreus, 2009, 17 (2):153-155, abstract only.
Plassmann, M. et al., "Trace Analytical Methods for Semifluorinated n-Alkanes in Snow, Soil, and Air," Analytical Chemistry, 2010, 82 (11):4551-4557.
Plassmann, M. et al., "Theoretical and Experimental Simulation of the Fate of Semifluorinated n-Alkanes During Snowmelt," Environmental Science & Technology, 2010, 44 (17):6692-6697.
Rosenberg, A.S., "Effects of Protein Aggregates: An Immunologic Perspective," The AAPS Journal, 2006, 8 (3):E501-E507.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Schnetler et al., "Lipid composition of human meibum: a review", S Afr Optom, 2013, 72(2):86-93.
Spöler et al., ""Towards a New in vitro Model of Dry Eye: The ex vivo Eye Irritation Test"", Developments in Ophthalmology, 2010, 45:93-107.
Steven, P. et al. "Semifluorinated Alkane Eye Drops for Treatment of Dry Eye Disease—A Prospective, Multicenter Noninterventional Study" Journal of Ocular Pharmacology and Therapeutics (2015) vol. 31, No. 8, pp. 498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Tiffany, J.M., "Individual Variations in Human Meibomian Composition", Exp. Eye Res., 1978, 27:289-300.
Troiano et al., "Effect of Hyptonic .4% Hyaluronic Acid Drops in Dry Eye Patients: A Cross-Study", Cornea 27(10): 1126-1130 (Abstract Only).
Wang, W., "Lyophilization and Development of Solid Protein Pharmaceuticals," International Journal of Pharmaceutics, 2000, 203:1-60.
"What is retinal vitrectomy?", Presented by: Medical Online, Obesity and Diabetes Mellitus, 2005, 4(2):284-286 (3 pages).
Wong, D. et al., "Perfluorocarbons and Semifluorinated Alkanes," Seminars in Ophthalmology, 2000, 15 (1):25-35.
Xalatan, Latanoprost Ophthalmic Solution, 50 µg/mL Prostaglandin F 2α analogue, Product Monograph, Jul. 21, 2014, 30 pages.
Zhang et al., "Surface micelles of semifluorinated alkanes in Langmuir-Blodgett monolayers," Phys. Chem. Chem. Phys., 2004, 6:1566-1569.
Agrahari, et al., "A comprehensive insight on ocular pharmacokinetics," Drug Delivery and Translational Research, 2016, 6(6):735-754.
Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.

(56) References Cited

OTHER PUBLICATIONS

Lin, H. et al., "Dry eye disease: A review of diagnostic approaches and treatments," Saudi Journal of Ophthalmology, 2014, 28:173-181.

Martín-Montañez et al., "End-of-day dryness, corneal sensitivity and blink rate in contact lens wearers," Cont Lens Anterior Eye, 2015, 38(3):148-51.

Novaliq GmbH Begins Phase II Clinical Trial of Cyclasol for the Treatment of Moderate to Severe Dry Eye Disease, (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.

Scherer et al., "Eyesol: A Novel Topical Ocular Drug Delivery System for Poorly Soluble Drugs," Drug Development & Delivery, 2013, vol. 13, No. 1, pp. 40-44.

Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729 (Abstract Only), 1 page.

Wirta, David L. et al., "A Clinical Phase II Study to Assess Efficacy, Safety and Tolerability of Waterfree Cyclosporine Formulation for the Treatment of Dry Eye Disease," *Ophthalmology*, 2019, 126:792-800.

\* cited by examiner

SEMIFLUORINATED ALKANE COMPOSITIONS

CROSS REFERENCE TO RELATED APPLICATIONS

This application is a divisional application of U.S. patent application Ser. No. 16/041,317, filed on Jul. 20, 2018, which is a continuation of U.S. patent application Ser. No. 15/428,031, filed on Feb. 8, 2017, which is a continuation of U.S. patent application Ser. No. 14/427,969, filed on Mar. 12, 2015, which application is a National Stage Entry under 35 U.S.C. § 371 of International Application No. PCT/EP2013/068909, filed Sep. 12, 2013, which claims priority to European Patent Application No. 12183997.1, filed Sep. 12, 2012, and European Patent Application No. 13169399.6, filed May 27, 2013, the contents of each of which are incorporated herein by reference in their entireties.

FIELD

The present invention is in the field of compositions comprising oxidation-prone pharmaceutically active ingredients, specifically compositions that are based on semifluorinated alkanes. In particular, the compositions of the present invention may be topical ophthalmic compositions useful in the treatment of ocular diseases or conditions.

BACKGROUND

The stability of an active pharmaceutical compound during storage over a variety of conditions is a generally of concern during development of a formulation for the compound. This aspect is especially relevant for liquid formulations of compounds which are sensitive and/or prone to decomposition via oxidation pathways. It is becoming even more relevant today as countries with hot and moderately humid climate (i.e. ICH zone IVb countries) are becoming increasingly important to pharmaceutical companies so that new drug formulations are needed which take into account the higher temperatures and humidifies of these countries.

Oxidation may be promoted thermally, photolytically, or by chemical means. Compounds comprising aliphatic double bond systems are, in particular, sensitive towards degradation by oxidation, often via free-radical chain processes with molecular oxygen.

Such processes, known also as auto-oxidation, generally begins via an initiation process in which a free-radical is generated (e.g. via abstraction of a hydrogen atom by an initiator radical), followed by propagation steps involving oxygen and further compound molecules. Termination may occur when two radical products couple. Compounds comprising free-radical stabilizing aliphatic double bond configurations such as the methylene-interrupted polyene systems of polyunsaturated lipid derivatives are generally more susceptible to auto-oxidation. These and other oxidation processes can readily lead to, over time, the formation and accumulation of undesirable and pharmaceutically ineffective reaction products. Some of the degradants may be harmful or toxic.

The use of antioxidants and/or stabilizer excipients remains one of the foremost strategies for mitigating or preventing the oxidation of such compounds and to increase shelf-life. Typical antioxidants are butylated hydroxytoluene (BHT), ascorbic acid, tocopherol derivatives etc. Many antioxidants will act as free-radical scavengers; and act by terminating free-radicals and inhibiting the chain processes. Excipients which can act as metal ion chelators e.g. ethylene diamine tetraacetic acid (EDTA) may also be used to limit the effect of trace heavy metal impurities which can also catalyse oxidation reactions. The encapsulation or shielding of oxidation-sensitive compounds, such as with liposomes or cyclodextrins are also known methods of preventing degradation.

A further measure to prevent oxidative degradation of such compounds would be the removal of oxygen dissolved in the liquid vehicle through sparging with an inert gas, with for example, nitrogen. This is however process-intensive and not cost-effective, and requires, in addition, special attention during further processing steps and with packaging to prevent the reintroduction of atmosphere.

Polyunsaturated fatty acids (often abbreviated as PUFA) are a class of compounds that are prone to oxidative degradation. These include omega fatty acids such as omega-3 fatty acids (also known as (n-3 fatty acids or n-3 fatty acids) and omega-6 fatty acids (also known as (n-6 fatty acids or n-6 fatty acids). These are essential fatty acids because they are available only through dietary intake, and because they involved in many human metabolic processes and functions. As such, they have been implicated as beneficial in the treatment or prophylaxis of a wide variety of different health conditions.

For example, these compounds have been found to be useful for the topical treatment and prevention of ocular pathologies such as dry eye disease (DED). DED, also known as keratoconjunctivitis sicca or dysfunctional tear syndrome, is a multifunctional disorder of the tear film and ocular surface which results in discomfort, visual disturbance, and often even in ocular surface damage. The loss in dynamic stability of the structure, composition, volume and distribution, as well as clearance of the tear film can lead to the development of DED.

An inflammation cycle is one of the key processes that maintain and potentially progress the dry eye condition. Omega fatty acids, in relation to their anti-inflammatory properties, have been found to reduce the severity of DED and its symptoms and improve tear secretion. Omega-3 fatty acids, in particular, have been associated with the modulation of the production of anti-inflammatory and immunomodulatory eicosanoid prostaglandins such as PGE1. They are also implicated in suppressing the expression of pro-inflammatory cytokines such as IL-1 and TNF-α, which are associated with dry eye disease.

The formulation of such active ingredients prone to oxidation into topical ophthalmic compositions such as eye drops can however be challenging. The choices of excipients, and therefore antioxidants and stabilizers which can be used are more limited due to incompatibility, toxicity or poor tolerance with the ocular surface. At the same time, however, the minimization of degradation (resulting in colour changes of the preparation, precipitation of insoluble materials, etc.) becomes more acute.

Compositions comprising omega fatty acids for the topical treatment of the dry eye condition and its symptoms are however known in the art. Gastrointestinal intolerance resulting from the oral ingestion of large quantities of these fatty acids as supplements (and systemic absorption effect) can be avoided with direct and local administration of these active molecules to the surface of the eye.

For example, Remogen® Omega (marketed by TRB Chemedica International S.A.), is a commercially available ophthalmic preparation comprising omega fatty acids that indicated for dry eye conditions. As disclosed in its product information, the preparation is a hypotonic hydrogel containing eicosapentaenoic acid (EPA) and docosahexaenoic acid (DHA), antioxidant vitamin E (tocopheryl acetate), the emollient substances carbopol 980, glycerol, pemulen, and sodium hydroxide, disodium phosphate, and distilled water. The hydrogel composition itself is described as a microemulsion, with a dispersion of the lipidic molecules (fatty acids and vitamin E). The product is packaged in the form of single-dose containers packed in an aluminium pouch, with the recommendation to discard the product immediately after use. With respect to stability, storage is suggested to be in a refrigerator at 2-8° C., with a shelf-life of 3 months if stored, at below 25° C., unrefrigerated. Due to its poor thermal stability, the product is shipped in a cold chain, i.e. transported in refrigerated containers and stored at the warehouse and in the pharmacy under refrigeration. Thus the consignment is expensive and requires a substantial effort in terms of temperature monitoring and logistics.

Similar, if not the same type of ophthalmic hydrogel compositions are also disclosed in US 2012/0010280. It is described that the fatty acids are in solution in the antioxidant tocopheryl acetate, with the tocopheryl acetate present in amounts of up to 75% by weight of the oily mixture. These are dispersed as oily droplets in the hydrogel. Aqueous emulsions comprising a combination of omega-3 and omega-6 fatty acids, and surfactant (e.g. Tween 80), Glucam E-20, and a drop of vitamin E as an antioxidant were found to be poorly adapted for maintaining stability of the omega fatty acids are proposed in WO 2006/007510. It should be noted, however, that emulsion systems based on hydrogels, with their generally increased viscosity and bioadhesive properties may incur, upon instillation and also during its contact time to the ocular surface, irritating foreign body sensation and blurred vision. Depending also on the degree of their viscosity, these may be more difficult to dispense and administer.

In general, one of the major disadvantages of formulations based on emulsions system is that in contrast to single phase systems, emulsion systems may be more complex and difficult to manufacture, especially in sterile form. Frequently, they are not readily sterilisable by thermal treatment without negative impact on their physical properties. Emulsions are also inherently unstable, and could phase separate with time or fluctuations in storage conditions. They, as with all aqueous based systems, are more prone to microbial contamination during use as well. The aseptic processing of emulsions is complex, costly, and is associated with higher risks of failure, i.e. microbial contamination.

Retinoid (Vitamin A) derivatives are another class of hydrocarbon compounds comprising high levels of polyunsaturation, and which are also prone to degradation via oxidation pathways. Retinoid derivatives include retinol, retinal, retinoic acid, tretinoin, isotretinoin, alitretinoin, and related derivatives. Vitamin A derivatives have been used for the treatment of inflammation in relation to the cornea, conjunctiva and other mucosal and epithelial tissues, including conditions such as dry eye disease.

US2012/0095097 for example discloses aqueous ophthalmic compositions comprising Vitamin A, at least 0.4 w/v % of polyoxyethylene polypropylene glycol and trometamol. Antioxidants such as dibutylhydroxytoluene and α-tocopherol acetate, may also be present in these compositions. These compositions are based on micelles of Vitamin A, which is presumably shielded and stabilized by non-ionic surfactant polyoxyethylene polypropylene glycol. These compositions are not preserved as such.

In principle, these preparations would require, if they were to be presented in multi-dose containers which are in principle more cost-efficient and convenient for patients than single-use vials, preservation in order to ensure their microbiological quality. The same would be applicable to all aqueous-based preparations. At the same time however, preservatives which can be used in ophthalmic formulations are potentially damaging to the eye, in particular to the ocular surface, and should be avoided especially in the context of dry eye disease. At least in earlier years, multi-dose formulations for ophthalmic administration had to be preserved using a physiologically acceptable preservative in order to reduce the risk of microbial contamination and infection.

Most preservatives are however problematic for DED patients in that they have a potential to negatively affect the ocular surface, thus counteracting the therapeutic intent. This is particularly relevant for patients with moderate to severe dry eye disease symptoms who may require frequent use for symptom relief, as well as patients who require multiple preserved topical medicaments.

As an alternative, single-dose containers are the main option for the administration of non-preserved formulations such as those used for the Remogen® Omega product. These are however less cost-efficient and convenient to handle for the patient than the conventional multi-dose bottle. Whilst ophthalmic formulations utilizing 'vanishing' preservatives such as sodium chlorite or sodium perborate, which can convert to non-toxic ions and water after instillation and contact with the tear film may also be an option, these may still be irritating to patients especially those with severe disease who may not have sufficient tear volume to effectively degrade the preservatives.

WO 2011/073134 discloses ophthalmic topical pharmaceutical compositions comprising immunosuppressant macrolides such as ciclosporin A and semifluorinated alkanes, for treatment of keratoconjunctivitis sicca. The semifluorinated alkanes in the disclosed compositions serve as suitable liquid vehicles for delivering the therapeutic pharmaceutical agent to the eye, and in particular have a high capacity for dissolving extremely challenging poorly soluble compounds such as ciclosporin. However, there is no mention of the ability of semifluorinated alkanes to stabilize oxidation-sensitive compounds over an extended period of time.

It is therefore an object of the present invention to provide a novel composition which comprising one or more active compounds comprising more than one aliphatic double bond prone to oxidation, and which at the same time addresses and overcomes the various issues and at least one of the limitations or disadvantages associated with prior art formulations. In a specific aspect, it is an object of the invention to provide an ophthalmic composition for the treatment or prevention of a condition or disease such as dry eye or conditions relating to the inflammation of the ocular tissue. In a further aspect, it is an object of the invention to provide a method of stabilizing an active compound with more than one aliphatic double bond prone to oxidation which does not exhibit one or more of the disadvantages of prior art. Further objects of the invention will become clear on the basis of the following description, examples, and patent claims.

SUMMARY OF THE INVENTION

In a first aspect, the present invention provides a stable liquid composition comprising an active compound with more than one aliphatic double bond prone to oxidation, wherein the active compound is dissolved, dispersed or suspended in a liquid vehicle comprising a semifluorinated alkane of formula $F(CF_2)_n(CH_2)_mH$ or of formula $F(CF_2)_n$ $(CH_2)_m(CF_2)_oF$, wherein n, m, and o are integers independently selected from the range of 3 to 20. The liquid vehicle is substantially free of water.

In one of the embodiments, the composition of the invention comprises a polyunsaturated fatty acid or derivative thereof, in particular an ester derivative. It is further preferred that the polyunsaturated fatty acid or derivative is selected from an omega-3 or omega-6 fatty acid or derivative, such as an omega-3 or omega-6 fatty acid ester, or a mixture thereof. In a further preferred embodiment, said omega-3 or omega-6 fatty acids are selected from docosahexaenoic acid or eicosapentaenoic acid and ester derivatives thereof.

In a further aspect, the invention provides the use of such compositions as a medicament, wherein the medicament may be topically administered to the eye or ophthalmic tissue, and/or wherein the medicament may be used for the treatment of a condition or disease of an eye or ophthalmic tissue such as inflammatory conditions of the ophthalmic tissue or keratoconjunctivitis sicca (dry eye).

In yet a further aspect, the invention provides a method of stabilizing an active compound with more than one aliphatic double bond prone to oxidation comprising the step of dissolving, dispersing, suspending the active compound in a liquid vehicle comprising a semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20, and wherein the liquid vehicle is substantially free of water. In one of the preferred embodiments, the active compound is an omega-3 or an omega-6 fatty acid or an ester derivative thereof.

DETAILED DESCRIPTION OF THE INVENTION

In a first aspect, the invention provides a stable liquid composition comprising an active compound with more than one aliphatic double bond prone to oxidation. The composition is further characterized in that the active compound is dissolved, dispersed or suspended in a liquid vehicle comprising a semifluorinated alkane as defined in claim 1 and further explained below As used herein, an active compound refers to any type of pharmaceutically, nutraceutically or otherwise health-promoting active compound or derivative that is useful in the prevention, diagnosis, stabilization, treatment, or—generally speaking—management of a condition or disease. A therapeutically effective amount refers to a dose, concentration or strength which is useful for producing a desired pharmacological, nutraceutical or otherwise health-promoting or—supporting effect.

Active compounds with more than one aliphatic double bond prone to oxidation are usually susceptible to degradation and deterioration over time and storage. The aliphatic double bonds of these compounds are featured in configurations that are particularly prone to undergo oxidation reactions, leading to the formation of side products and quantitative loss of active compound over time. The present invention provides methods of stabilizing such active compounds against oxidation, in particular oxidation which may occur and/or be promoted by thermal, photolytic or chemical means, and in the presence of oxygen as may be present in the atmosphere or as introduced to an initially inert environment over time.

As used herein, an aliphatic double bond refers to a carbon-carbon double bond (C=C). An active compound with more than one such double bond may have at least two aliphatic double bonds, in particular in a configuration wherein the double bonds are separated by a methylene group (—$CH_2$—). The one or more aliphatic double bonds of the active compounds of the invention may be in the cis (Z) or trans (E) configuration, or combinations thereof. In one embodiment, the active compound of the invention comprises a structural component of the formula —(HC=CH—$CH_2$—HC=CH)$_x$—, wherein x is an integer ranging from 2 to 10, in particular from 2 to 5.

Active compounds with more than one aliphatic double bond in which the double bonds are separated by a bridging methylene group (also commonly referred to as compounds possessing methylene-interrupted polyenes) include polyunsaturated fatty acids. Polyunsaturated fatty acids are linear carboxylic acids possessing carbon chains with more than one carbon-carbon double bond. These lipophilic lipids are prone to oxidation, especially in the presence of atmospheric oxygen via radical initiated auto-oxidation processes. In an embodiment, the compositions of the invention comprise a polyunsaturated fatty acid with number of carbon atoms ranging from C16 to C24. Derivatives of polyunsaturated fatty acids, such as esters and in particular alkyl esters are within the scope of the invention. It should be understood within the context of the present invention that a reference to any polyunsaturated fatty acid, or group or species thereof, also covers the respective derivatives, in particular the esters, even if not specifically mentioned.

Polyunsaturated fatty acids (often abbreviated as PUFA) include omega fatty acids such as omega-3 fatty acids (also known as ω-3 fatty acids or n-3 fatty acids) and omega-6 fatty acids (also known as ω-6 fatty acids or n-6 fatty acids). Examples of omega-3 fatty acids (also known as ω-3 fatty acids or n-3 fatty acids) include eicosapentaenoic acid (EPA), docosahexaenoic acid (DHA), α-linolenic acid (ALA). Examples of omega-6 fatty acids (also known as ω-6 fatty acids or n-6 fatty acids) include gamma-linolenic acid, linoleic acid, dihomo-gamma-linolenic acid. Derivatives of omega-3 fatty acids or omega-6 fatty acids, such as ester or alkyl ester derivatives are also within the scope of the invention. Particularly preferred alkyl ester derivatives are eicosapentaenoic acid ethyl ester or docasahexaenoic acid ethyl ester. Derivatives of eicosapentaenoic acid or docosahexaenoic acid such as resolvins and neuroprotectins are also suitable as active compounds within the scope of the invention.

In a further embodiment, the active compounds with more than one aliphatic double bond prone to oxidation are compounds comprising a structural component with more than one aliphatic double bond in linear conjugation with one another. Active compounds comprising more than one aliphatic double bond in linear conjugation are also commonly referred to as polyenes. Preferably, the active compound comprises at least three, or more preferably four or five linearly conjugated double bonds Preferably, the active compounds structurally comprise a conjugated triene, tetraene, pentaene, hexaene or heptaene component. In one embodiment, the active compound comprising a polyene component may be a macrocycle, wherein the polyene or the linearly conjugated double bonds form part of the cyclic structure. The one or more linearly conjugated aliphatic double bonds may be in the cis (Z) or trans (E) configuration, or combinations thereof.

Examples of active compounds comprising more than one linearly conjugated double bond include, but are not limited to, lipophilic vitamin derivatives such as retinoids and derivatives thereof. This class of compounds are also unstable towards prolonged storage and prone to degradation through oxidative pathways such as auto-oxidation. Retinoids and retinoid derivatives (also often referred to as Vitamin A derivatives) include retinol, retinoic acid and its esters (e.g. retinol palmitate or retinol acetate), retinal, tretinoin, isotretinoin, and alitretinoin.

Further examples of active compounds also comprising linearly conjugated double bond systems sensitive and or prone to radical-mediated oxidative degradation with oxygen include sirolimus (rapamycin), a macrolide immunosuppressant drug compound whose structure contains three contiguous double bonds.

Moreover, polyene compounds are contemplated as oxidation-sensitive active ingredients according to the invention, in particular polyene antifungals. In one embodiment, the composition comprises a polyene antifungal such as nystatin, natamycin or amphothericin dissolved in a liquid carrier substantially consisting of one or more semifluorinated alkanes as described herein.

The compositions of the invention may optionally further comprise a carotenoid or carotenoid derivative, in particular a xanthophyll. These compounds also possess poly-conjugated double bond systems. Particularly preferred are lutein and zeaxanthin. Derivatives of lutein or zeaxanthin, such as lutein or zeaxanthin esters are also considered. In a particular embodiment, liquid compositions comprising at least two or more semifluorinated alkanes further comprise lutein or a derivative thereof.

In a further embodiment, the composition comprises ciclopirox olamine as active ingredient. Preferably, ciclopirox olamine is incorporated in the dissolved state. As will be discussed in more detail below, some of the key advantages of the present invention are brought about by the presence of a semifluorinated alkane in the composition as liquid vehicle, or part of the liquid vehicle, for active compounds such as polyunsaturated fatty acids, retinoids, or other active compounds with more than one aliphatic double bond prone to oxidation.

Semifluorinated alkanes are linear or branched alkanes some of whose hydrogen atoms have been replaced by fluorine. In a preferred embodiment, the semifluorinated alkanes (SFAs) used in the present invention are composed of at least one non-fluorinated hydrocarbon segment and at least one perfluorinated hydrocarbon segment. Particularly useful are SFAs which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFAs having two or three segments as RFRH and RFRHRF, respectively, wherein $R_F$ designates a perfluorinated hydrocarbon segment, $R_H$ designates a non-fluorinated segment. Alternatively, the compounds may be referred to as FnHm and FnHmFo, respectively, wherein F means a perfluorinated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are integers independently selected from the range of 3 to 20. SFAs which are useful in the context of the present invention are also described in EP-A 965 334, EP-A 965329 and EP-A 2110126, the disclosure of which documents is incorporated herein.

In a further embodiment, the compositions of the invention comprise a semifluorinated alkane according to the formula $F(CF_2)_n(CH_2)_mH$, wherein n and m are integers independently selected from the range of 3 to 20. In another particular embodiment, n is an integer from the range of 3 to 8 and m is an integer from the range of 3 to 10. In yet another particular embodiment, the semifluorinated alkane is a compound according to the formula $F(CF_2)_n(CH_2)_mH$ wherein n is an integer from the range of 6 to 20 and m is an integer from the range of 10 to 20. Most preferably, the semifluorinated alkane is a liquid. Preferred SFAs include, in particular, the compounds $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, and $F(CF_2)_6(CH_2)_{10}H$. Further preferred SFAs include, in particular, $F(CF_2)_8(CH_2)_{10}H$ and $F(CF_2)_{10}(CH_2)_{12}H$.

In a further embodiment, the composition may comprise more than one SFA. Preferably, compositions comprising more than one SFA comprise at least one of SFAs selected from $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, and $F(CF_2)_6(CH_2)_{10}H$. In another embodiment, the composition comprises at least two SFAs selected compounds $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, and $F(CF_2)_6(CH_2)_{10}H$, and at least one of $F(CF_2)_3(CH_2)_{10}H$ and $F(CF_2)_{10}(CH_2)_{12}H$. In one of the preferred embodiments, the composition comprises a first semifluorinated alkane of formula $F(CF_2)_n(CH_2)_mH$, wherein n is an integer from the range of 3 to 8 and m is an integer from the range of 3 to 10 and a second semifluorinated alkane of the formula $F(CF_2)_n(CH_2)_mH$ wherein n is an integer from the range of 6 to 20 and m is an integer from the range of 10 to 20.

As mentioned, the compositions comprise an active compound with more than one aliphatic double prone to oxidation, wherein the active compound is dissolved, dispersed or suspended in a liquid vehicle comprising a SFA that is substantially free of water. In some embodiments, the liquid vehicle comprising a SFA may further comprise other organic liquids or other excipients, but is effectively free of water.

According to a particular embodiment, the active compounds of the invention may be dissolved, that is, in complete solvation or solution in a liquid vehicle comprising a semifluorinated alkane. Alternatively, the active compounds may be dispersed or suspended in a liquid vehicle comprising a semifluorinated alkane. As used herein, dispersing means the formation of a system having at least one continuous (or coherent) phase and at least one discontinuous (or inner) phase which is dispersed in the continuous phase. The term dispersion is understood to include colloidal systems in which the active compound is finely dispersed in the liquid phase. It is also understood that a suspension is a type of dispersion, in which the dispersed phase is in the solid state. The suspensions useful for practicing the invention are liquids, at least at physiological temperature, which means that the continuous phase is liquid. Typically, suspensions are liquid at room temperature.

Liquid SFAs are chemically and physiologically inert, colourless and stable. Their typical densities range from 1.1 to 1.7 g/cm³, and their surface tension may be as low as 19 mN/m. SFAs of the $F(CF_2)_n(CH_2)_mH$ type are insoluble in water but also somewhat amphiphilic, with increasing lipophilicity correlating with an increasing size of the non-fluorinated segment. Liquid SFAs of this type are being used commercially for unfolding and reapplying a retina, for long-term tamponade as vitreous humor substitute (H. Meinert et al., European Journal of Ophthalmology, Vol. 10(3), pp. 189-197, 2000), and as wash-out solutions for residual silicon oil after vitreo-retinal surgery. This and other applications have established SFAs as physiologically well tolerated compounds.

It has also been proposed that SFAs have high solubility for gases such as oxygen, and may act as oxygen carriers (U.S. Pat. No. 6,262,126). Experimentally, they have been used as blood substitutes, as oxygen-carriers (H. Meinert et al., Biomaterials, Artificial Cells, and Immobilization Biotechnology, Vol. 21(5), pp. 583-95, 1993).

In contradiction to such facts and teachings, the inventors have found that liquid compositions comprising SFAs and the oxidation-sensitive active compounds, such as those described above, are surprisingly stable under ambient as well as non-ideal conditions (as illustrated by the examples further below).

The inventors have found that a method of stabilising a compound of the invention can simply comprise the step of dissolving, dispersing, or suspending an active compound of the invention in a liquid vehicle comprising a semifluorinated alkane, as no additional antioxidants or other active compound stabilizers, as are typically used for the formulation of such compounds are required. This simplification can be advantageous for various medical uses of the composition involving especially, frequent administration to tissues such as ocular or mucosal tissues. These generally have poor tolerability to a wide variety of antioxidants and stabilizers and generally do not benefit from frequent exposure to such excipients.

In one embodiment, a method of stabilising a polyunsaturated fatty acid or an ester derivative thereof comprises the step of dissolving, dispersing or suspending the polyunsaturated fatty acid or an ester derivative thereof in a liquid vehicle comprising a semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20 and wherein the liquid vehicle is substantially free of water. In yet a further embodiment, said method of stabilisation comprises the step of dissolving, dispersing, or suspending a polyunsaturated fatty acid selected from an omega-3 or an omega-6 fatty acid or ester derivatives, or mixtures thereof in a liquid vehicle comprising a semifluorinated alkane selected from $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_3H$, and $F(CF_2)_6(CH_2)_{10}H$.

Further embodiments within the scope of the invention are stable liquid compositions consisting of essentially one or more omega-3 fatty acids or derivatives thereof dissolved or dispersed in a liquid semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20 and wherein the liquid vehicle is substantially free of water. Compositions comprising no further active compounds other than omega-3 fatty acid or derivatives thereof are also within the scope of the invention. Preferred are stable liquid compositions consisting of one or more omega-3 fatty acid selected from α-linolenic acid, docosahexaenoic acid, or eicosapentaenoic acid and ester derivatives thereof, wherein the omega-3 fatty acid or ester derivative thereof is dissolved or dispersed in a semifluorinated alkane of the invention, for instance, $F(CF_2)_6(CH_2)_8H$.

In a further preferred embodiment, the liquid composition consists essentially of docosahexaenoic acid and/or eicosahexaenoic acid or ester derivatives thereof dissolved in or dispersed in $F(CF_2)_6(CH_2)_8H$.

In a particular embodiment, liquid compositions comprising at least two or more semifluorinated alkanes further comprise one or more omega-3-fatty acid or omega-3-fatty acid derivative, and/or omega-6 fatty acid or omega-6 fatty acid derivative.

Also contemplated are methods of stabilizing a retinoid selected from retinol, retinoic acid, retinal, tretinoin, isotretinoin, and alitretinoin or derivatives thereof, or sirolimus, or a polyene compound, or ciclopirox olamine, comprising the step of dissolving, dispersing or suspending said compounds in a liquid vehicle comprising a semifluorinated alkane of formula $F(CF_2)_n(CH_2)_mH$ or of formula $F(CF_2)_n(CH_2)_m(CF_2)_oF$, wherein n, m, and o are integers independently selected from the range of 3 to 20 and wherein the liquid vehicle is substantially free of water. In another embodiment, method of stabilising a retinoid selected from retinol, retinoic acid, retinal, tretinoin, isotretinoin, and alitretinoin or derivatives thereof, or sirolimus, comprises the step of dissolving, dispersing or suspending said compounds in a liquid vehicle comprising a semifluorinated alkane selected from $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, and $F(CF_2)_6(CH_2)_{10}H$.

In a further embodiment of the invention, liquid compositions comprising at least two or more semifluorinated alkanes further comprise at least one solubilized lipophilic vitamin or vitamin derivative.

The liquid compositions comprising an active compound with more than one aliphatic double bond prone to oxidation dissolved, dispersed or suspended in a liquid vehicle comprising a semifluorinated alkane as described previously, wherein the liquid vehicle is substantially free of water may comprise at least about 0.01-10 wt. % of active compound. Preferably, the compositions comprise at least about 1 wt. % of active compound relative to the weight of the composition, such as about 2 wt % or more, or at least 5 wt %.

The compositions of the present invention are useful as medicaments, in particular as medicaments topically administered to an eye or ophthalmic tissue, to the skin, or to the buccal, anal, vaginal, or nasal mucosa.

The SFA component of the liquid vehicle of these compositions exhibit properties rendering them particularly amenable for ophthalmic applications. Many of the SFAs as defined herein have refractive indices close to water. In one of the specific embodiments, the invention is therefore practised with an SFA whose refractive index is from 1.29 to 1.35, and in particular from about 1.30 to about 1.35 at 20° C.

Moreover, SFAs according to the invention exhibit a remarkable wetting and spreading behaviour by which they can rapidly and effectively spread over the corneal surface and conjunctiva. Wetting means the ability of a liquid to establish and maintain contact with a solid surface, resulting from intermolecular interactions when the two are brought together. The balance between adhesive and cohesive forces determines the degree of wetting. The higher the adhesive forces compared to the cohesive forces, the more a drop of liquid will spread across the surface of the solid material. Conversely, very high cohesive forces within the liquid will cause the drop to form a sphere, thus avoiding contact with the surface. Similarly, spreading may also occur at the interface of two liquids which are brought into contact with each other.

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

A low contact angle of less than 90° indicates high wettability and/or spreading, whereas a higher contact angle indicates poor wettability and spreading. Perfect wetting and spreading results in a contact angle of 0°, also reported as no measurable contact angle.

SFAs according to the invention exhibit excellent wetting of various surfaces. For example, the contact angle of both F4H5 and F6H8 on tablets compressed from either trospium chloride or fenofibrate (150 mg of drug substance compressed at 15-20 kN to tablets of 13 mm in diameter) is not measurable, i.e. there is perfect wetting. It is noted that fenofibrate is an example of a hydrophobic, poorly water-soluble compound, whereas trospium chloride is hydrophilic and water-soluble. For comparison, the contact angle of purified water on the fenofibrate tablet was determined as 92.5°, i.e. the tablet was poorly wetted by water.

In addition, SFAs according to the invention are also capable of forming very small droplets when dispensed from a dropper such as an eye dropper. Without wishing to be bound by theory, it is believed that the small droplet size is a result of an interplay of the SFA's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct.

The invention also provides a means of formulating non-aqueous ophthalmic compositions which are microbiologically stable. Aqueous ophthalmic compositions are prone to bacterial contamination. In comparison, SFAs according to the invention have bacteriostatic properties and do not support microbial growth. Hence, it is possible to formulate preservative-free ophthalmic compositions which are better tolerable for many patients suffering from eye conditions that are readily exacerbated by preservatives or other excipients that may irritated through repeated exposure.

The compositions of the invention are thus very well suited for the topical administration to an eye or ophthalmic tissue. Ophthalmic tissue includes any surface of the eye anatomy that is, or can be (i.e. by non-surgical means) topically exposed. Preferably, the compositions are administered to the cornea or conjunctiva. The compositions are also preferably administered to the upper or lower eye lid margins, meibomian gland ducts, eyelashes or any area of the eye or eye lid anatomy.

In particular, it is contemplated that these compositions can be used for the treatment of a condition or disease of an eye or ophthalmic tissue, such as inflammatory conditions of the ophthalmic tissue or keratoconjunctivitis sicca (dry eye) or symptoms or conditions associated therewith. According to an embodiment of the invention, a composition consisting of a semifluorinated alkane of the formula $F(CF_2)_n(CH_2)_mH$, wherein n is an integer from the range of 3 to 8 and m is an integer from the range of 3 to 10, and optionally one or more further excipients may be used as a medicine in the treatment of keratoconjunctivitis sicca (dry eye) or a symptom or condition associated therewith Keratoconjunctivitis sicca is a complex, multifaceted disease or condition as described above. Aqueous-deficient DED, evaporative DED are within the scope of keratoconjunctivitis sicca and form specific subtypes thereof. Sjögren syndrome, lacrimal gland insufficiency, meibomian gland disease and meibomian gland dysfunction, and other conditions are also associated with keratoconjunctivitis sicca, being direct or indirect causes thereof, and may be treated with the composition of the invention.

Meibomian gland diseases cover a broad range of meibomian gland disorders including neoplasia and congenital disorders. Meibomian gland dysfunction, on the other hand is understood to be abnormalities of the meibomian glands which are often characterized by gland duct obstructions and/or changes (qualitative and/or quantitative) to the secretions of the glands. In general, conditions or disease states causing or leading to an abnormal, reduced or increased delivery of lipids to the tear film can give rise to keratoconjunctivitis sicca and the symptoms associated therewith.

Symptoms of keratoconjunctivitis sicca include a dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; excessive reflex tearing. In addition to the symptoms of keratoconjunctivitis sicca as described, patients with meibomian gland dysfunction may also experience symptoms including itchiness, redness, swelling, pain or soreness, discharge accumulation or crusting specifically at the lid margins. It is understood that not all patients suffering from keratoconjunctivitis sicca exhibit all symptoms simultaneously. Hence, there is currently no uniform set of criteria for diagnosing the disease. It is also understood that patients may suffer from one or more subtypes of keratoconjunctivitis sicca, or one or more conditions or disease pathways causing keratoconjunctivitis sicca. It is however important to note that, within the scope of the present invention, any of the aspects, symptoms or pathophysiological consequences of dry eye disease may be addressed.

The compositions of the invention may also comprise one or more active compounds and/or further excipients as are required or useful. In an embodiment, the compositions of the invention may further comprise an anti-inflammatory compound selected from the group of NSAIDs, corticosteroids, and immunomodulators. In particular, such compositions may be useful as a medicament for topical administration to an eye or ophthalmic tissue, especially as medicaments for treatment of inflammatory conditions of ophthalmic tissue or keratoconjunctivitis sicca (dry eye), or a symptom or condition associated therewith. Preferred immunomodulators are calcineurin inhibitors (e.g. cyclosporin or tacrolimus) or mTOR inhibitors (e.g. sirolimus). Preferred NSAIDS include flurbiprofen, diclofenac, indometacin, bromfenac, nepafenac, ketoprofen, and ketorolac and salts and derivatives thereof. Preferred corticosteroids include prednisolone, loteprednol, dexamethasone, hydrocortison, rimexolone, fluorometholone and salts and derivatives thereof. These further active compounds are preferably also dissolved or dispersed in a liquid semifluorinated alkane of the invention.

In another embodiment, the compositions of the invention may also further comprise one or more flavan-3-ols such as catechins. Catechin or catechin isomers (e.g. epicatechin) and derivatives (for example, ester derivatives of catechin) are particularly preferred.

In terms of further excipients, if any, especially preferred are those that are biocompatible and are tolerated by the eye, and which are liquid and/or soluble and miscible in SFAs In particular, excipients are preferably selected from lipids, oils, lubricants, lipophilic vitamins, viscosity agents, antioxidants, surfactants and mixtures of two or more thereof.

Examples of potentially useful lipids and oily excipients and which may be included in the compositions of the invention include triglyceride oils (e.g. soybean oil, olive oil, sesame oil, cotton seed oil, castor oil, sweet almond oil), mineral oil (e.g. petrolatum and liquid paraffin), medium chain triglycerides (MCT), oily fatty acids, isopropyl myristate, oily fatty alcohols, esters of sorbitol and fatty acids, oily sucrose esters, oily cholesterol esters, oily wax esters, glycerophospholipids, sphingolipids, or any oily substance which is physiologically tolerated by the eye. Any synthetic, semi-synthetic or natural oily excipients which mimic or are structurally analogous or related to the components naturally found in the tear film lipid layer are also within the scope of the invention.

Examples of potentially useful lipophilic vitamin excipients include vitamin E (e.g. α-tocopherol) and their derivatives (e.g. tocotrienols) and esters (e.g. tocopherol acetate or tocopherol TPGS). In an embodiment, liquid compositions of the invention may further comprise at least one lipophilic vitamin excipient that is completely solubilized.

Examples of potentially useful lubricants and/or viscosity agents include carboxymethyl cellulose, hydroxymethyl cellulose, hydroxypropyl cellulose, glycerol, polyvinyl alcohol, polyethylene glycol, propylene glycol, hyaluronic acid, hydroxypropyl guar.

In one of the embodiments, the composition of the invention is free of surfactants. In an alternative embodiment, and depending on the specific active ingredient to be formulated, a small amount of a physiologically acceptable surfactant may be incorporated. Potentially useful surfactant excipients include in particular non-ionic surfactants or amphiphilic lipids. Surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, and mixtures of two or more thereof.

The composition may of course comprise further excipients as required or useful such as acids, bases, electrolytes, buffers, solutes, stabilisers, synergists, and—if required in a particular case—a preservative. In one of the embodiments, however, the composition is free of preservatives.

The compositions may be formulated to be administered as a liquid solution, gel, suspension, or spray. They may be prepared by commonly known techniques for the manufacture of said liquid solutions, gels, suspensions, or sprays.

Furthermore, the invention provides a pharmaceutical kit comprising the composition as described above and a container holding the composition. Preferably, the container which contains the composition has a dispensing means such as a dropping device adapted for topically administering the composition to the eye of a patient.

The following examples serve to illustrate the invention; however, these are not to be understood as restricting the scope of the invention.

EXAMPLES

Example 1

Solutions of the omega-3 fatty acid esters, eicosapentaenoic acid ethyl ester (EPA-EE) and docosahexenoic acid ethyl ester (DHA-EE), were prepared in $F(CF_2)_6(CH_2)_8H$ at concentrations of 1.0 wt % and 5.0 wt %.

Solutions containing a mixture of 1 wt % each of DHA-EE and EPA-EE (total 2.0 wt % of active compound) and 5.0 wt % of a combination of the DHA-EE and EPA-EE, at a ratio of approx. 2:3 in $F(CF_2)_6(CH_2)_8H$ were also prepared. The solutions were filled in crimped vials and stored at 2-8° C., at 25° C./60% RH, and at 40° C./75% RH for the purpose of conducting a 6 month stability programme. The results obtained after a 13-week period are reported herein.

Samples were taken from the vials at intervals for GC analysis (See Tables 1-3 for result) of the compositions. The remaining percentages of other components detected by GC (FID) but not shown here in the tables are attributed to impurities already present in the original samples of omega-3 fatty ester or the SFA vehicle before formulation. No rise in the level of impurities was observed over the course of the stability program.

No significant observable changes in the content of the omega-3 fatty acid esters were detected under all temperatures tested. Results were more or less also comparable across different batches at all storage conditions. In the following tables, the content of the active ingredient is presented as percentage relative to the initial content.

TABLE 1

Content of active compound (%) after storage at 2-8° C.

| Compound | After 4 weeks |
| --- | --- |
| 1.0 wt % EPA-EE | 99.6 |
| 1.0 wt % DHA-EE | 99.5 |
| 5.0 wt % EPA-EE | 99.9 |
| 5.0 wt % DHA-EE | 101.5 |
| 2.0 wt % EPA-EE/DHA-EE | 100.2/99.7 |
| 5.0 wt % EPA-EE/DHA-EE | 100.3/99.5 |

TABLE 2

Content of active compound (%) after storage at: 25° C./60% RH

| Compound | After 4 weeks | After 13 weeks |
| --- | --- | --- |
| 1.0 wt % EPA-EE | 99.6 | 99.0 |
| 1.0 wt % DHA-EE | 99.6 | 99.4 |
| 5.0 wt % EPA-EE | 99.8 | 99.5 |
| 5.0 wt % DHA-EE | 99.8 | 103.2[1] |
| 2.0 wt % EPA-EE/DHA-EE | 100.2/99.6 | 100.5/98.6 |
| 5.0 wt % EPA-EE/DHA-EE | 101.1/98.0 | 103.5/92.6 |

[1]Slight increase probably due to impurities with elution times similar to DHA-EE

TABLE 3

Content of active compound (%) after storage at 40° C./75% RH

| Compound | 1 week | 2 weeks | 4 weeks | 8 weeks | 13 weeks |
| --- | --- | --- | --- | --- | --- |
| 1.0 wt % EPA-EE | 99.6 | 99.6 | 99.6 | 99.4 | 97.3 |
| 1.0 wt % DHA-EE | 99.9 | 99.8 | 99.8 | 99.6 | 99.1 |
| 5.0 wt % EPA-EE | 99.9 | 99.9 | 99.8 | 99.4 | 98.7 |

TABLE 3-continued

Content of active compound (%) after storage at 40° C./75% RH

| Compound | 1 week | 2 weeks | 4 weeks | 8 weeks | 13 weeks |
|---|---|---|---|---|---|
| 5.0 wt % DHA-EE | 99.9 | 100.0 | 100.0 | 99.9 | 100.0 |
| 2.0 wt % EPA-EE/ DHA-EE | 101.8/98.2 | 100.3/99.6 | 100.5/99.0 | 100.8/98.3 | 100.8/98.2 |
| 5.0 wt % EPA-EE/ DHA-EE | 100.9/98.3 | 101.0/98.0 | 101.6/96.6 | 103.1/93.1 | 105.4/88.4 |

The invention claimed is:

1. A stable liquid composition comprising an active compound with more than one aliphatic double bond, wherein the active compound is dissolved, dispersed or suspended in a liquid vehicle
wherein the liquid vehicle comprises a semifluorinated alkane of formula $F(CF_2)n(CH_2)mH$, wherein n is an integer from 3 to 8 and m is an integer from 3 to 10, and wherein the active compound is a polyene antifungal selected from nystatin, natamycin, and amphotericin; and wherein the composition does not comprise any additional antioxidant.

2. The composition according to claim 1, wherein the semifluorinated alkane is selected from $F(CF_2)_4(CH_2)_5H$, $F(CF_2)_4(CH_2)_6H$, $F(CF_2)_4(CH_2)_8H$, $F(CF_2)_6(CH_2)_4H$, $F(CF_2)_6(CH_2)_6H$, $F(CF_2)_6(CH_2)_8H$, and $F(CF_2)_6(CH_2)_{10}H$.

3. The composition according to claim 1, wherein the composition further comprises a lipid or oily excipient selected from triglyceride oils, mineral oil, medium chain triglycerides, oily fatty acids, isopropyl myristate, oily fatty alcohols, esters of sorbitol and fatty acids, oily sucrose esters, oily cholesterol esters, oily wax esters, glycerophospholipids, and sphingolipids.

4. The composition according to claim 1, wherein the active compound is dissolved in the liquid vehicle.

5. The composition according to claim 1, wherein the liquid vehicle is substantially free of water.

6. The composition according to claim 1, wherein the composition further comprises an anti-inflammatory compound selected from the group consisting of NSAIDs, corticosteroids, and immunomodulators.

7. A kit comprising the composition according to claim 1 and a container for holding said composition.

8. The kit according to claim 7, wherein the container has a dispensing means adapted for topically administering the composition to the eye of a patient in need thereof.

9. The composition according to claim 1, wherein the polyene antifungal is dissolved in the liquid vehicle which consists of the one or more semifluorinated alkanes.

10. The composition according to claim 1, wherein the composition is a liquid solution, gel, suspension or spray.

11. The composition according to claim 1, wherein the composition is free of preservatives and/or free of surfactants.

12. The composition according to claim 1, wherein the composition is a non-aqueous preservative-free ophthalmic composition that is microbiologically stable.

* * * * *